(12) United States Patent  
Spahn

(10) Patent No.: US 8,031,837 B2
(45) Date of Patent: Oct. 4, 2011

(54) X-RAY SYSTEM INCLUDING A WIRELESS HANDHELD MONITORING UNIT

(75) Inventor: Martin Spahn, Chicago, IL (US)

(73) Assignee: Siemens Aktiengesellschaft, Munich (DE)

( * ) Notice: Subject to any disclaimer, the term of this patent is extended or adjusted under 35 U.S.C. 154(b) by 64 days.

(21) Appl. No.: 11/702,797

(22) Filed: Feb. 6, 2007

(65) Prior Publication Data

US 2007/0189462 A1 Aug. 16, 2007

(30) Foreign Application Priority Data

Feb. 14, 2006 (DE) .......................... 10 2006 006 838

(51) Int. Cl.
H05G 1/08 (2006.01)
H05G 1/30 (2006.01)
(52) U.S. Cl. ........................................................ 378/91
(58) Field of Classification Search .................. 378/91, 378/115, 116, 196, 197, 198, 57
See application file for complete search history.

(56) References Cited

U.S. PATENT DOCUMENTS

| | | | | |
|---|---|---|---|---|
| 5,608,774 A * | 3/1997 | Polichar et al. | ............. | 378/98.8 |
| 5,877,501 A * | 3/1999 | Ivan et al. | ............. | 250/370.09 |
| 6,178,225 B1 * | 1/2001 | Zur et al. | ............. | 378/98.2 |
| 6,285,742 B1 * | 9/2001 | Haumann et al. | ............. | 378/116 |
| 6,433,341 B1 * | 8/2002 | Shoji | ............. | 250/370.09 |
| 6,630,676 B2 * | 10/2003 | Takemoto | ............. | 250/370.09 |
| 6,697,453 B1 * | 2/2004 | Mueller et al. | ............. | 378/72 |
| 6,707,879 B2 * | 3/2004 | McClelland et al. | ............. | 378/57 |
| 6,856,667 B2 * | 2/2005 | Ellengogen | ............. | 378/57 |
| 6,898,268 B2 * | 5/2005 | Makila et al. | ............. | 378/38 |
| 6,972,411 B2 * | 12/2005 | Schick et al. | ............. | 250/370.11 |
| 7,006,600 B1 * | 2/2006 | Krema et al. | ............. | 378/98.7 |
| 7,015,478 B2 * | 3/2006 | Yamamoto | ............. | 250/370.09 |
| 7,071,823 B2 * | 7/2006 | Boesch et al. | ............. | 340/568.1 |
| 7,123,682 B2 * | 10/2006 | Kotian et al. | ............. | 378/21 |
| 7,180,451 B2 * | 2/2007 | Silzer, Jr. | ............. | 343/702 |
| 7,247,859 B2 * | 7/2007 | Murphy et al. | ............. | 250/370.09 |
| 7,250,608 B2 * | 7/2007 | Ozeki | ............. | 250/370.08 |
| 7,309,159 B2 * | 12/2007 | Watanabe | ............. | 378/198 |
| 7,426,261 B2 * | 9/2008 | Spahn | ............. | 378/98.8 |

FOREIGN PATENT DOCUMENTS

DE 197 08 984 A1 10/1998
DE 101 18 745 C2 3/2003

* cited by examiner

*Primary Examiner* — Allen C. Ho

(57) ABSTRACT

For a simplified and particularly flexible control of an x-ray system having an x-ray source, an x-ray detector and a control and monitoring unit, the control and monitoring unit is designed to be mobile and portable and has means for controlling and monitoring the x-ray system. In particular, the portable control and monitoring unit has a computing unit, a data storage device, means for image processing, means for outputting and displaying imaging and/or system data and means for inputting data and/or instructions.

16 Claims, 3 Drawing Sheets

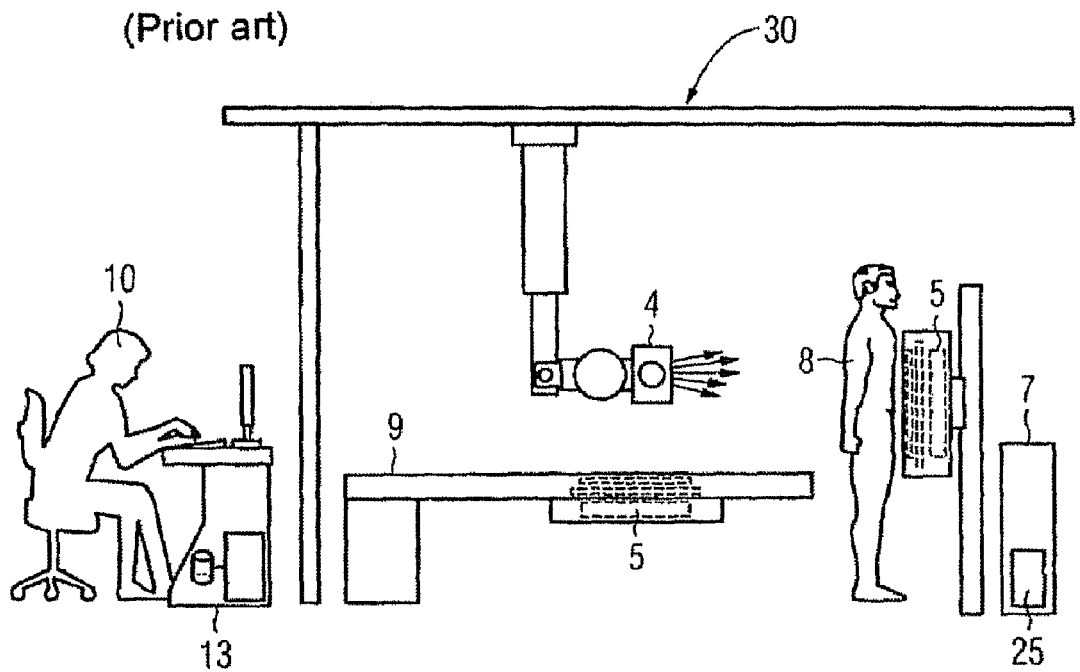
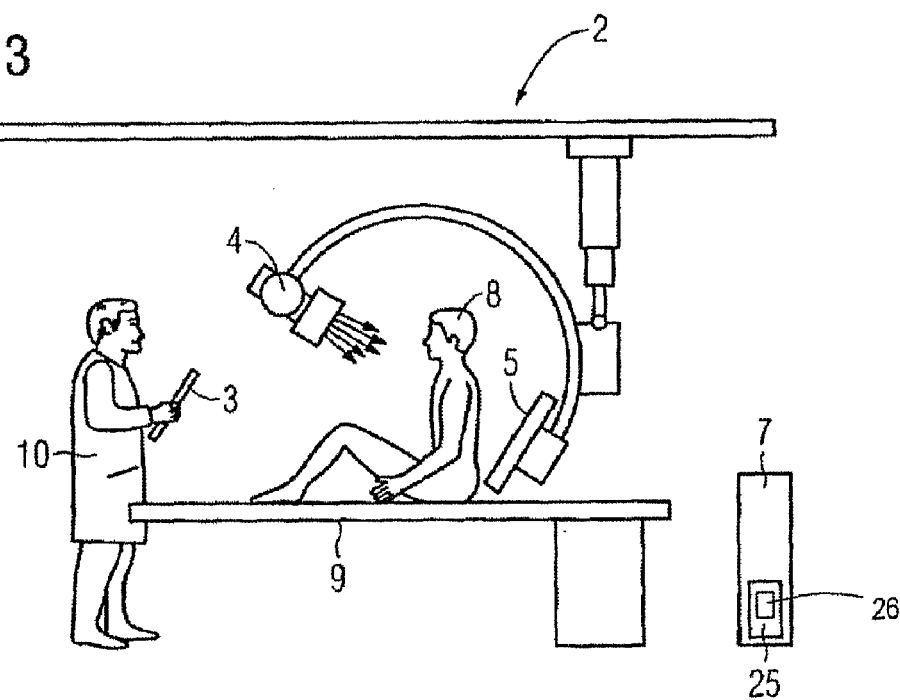

X-RAY SYSTEM INCLUDING A WIRELESS HANDHELD MONITORING UNIT

CROSS REFERENCE TO RELATED APPLICATIONS

This application claims priority of German application No. 10 2006 006 838.6 filed Feb. 14, 2006, which is incorporated by reference herein in its entirety.

FIELD OF THE INVENTION

The invention relates to an x-ray system, having an x-ray source, an x-ray detector and a control and monitoring unit.

BACKGROUND OF THE INVENTION

The provision of operating units for operating x-ray systems separately from the x-ray source, x-ray detector and the control unit is known, said operating units having both actuators for adjusting recording parameters as well as a display for indicating recording and system data. It is further known to design an operating unit to be flexible in the form of a remote controller. A flexible operating unit of this type is known for instance from DE 197 08 984 A1.

Furthermore, x-ray systems are known, which have control apparatuses in the form of moveable equipment trolleys, to which the x-ray source can also be attached for instance. An x-ray system of this type is known from DE 101 18 745 C2 for instance.

SUMMARY OF THE INVENTION

The object of the present invention is thus to further improve the flexibility of x-ray systems of this type.

The object is achieved in accordance with the invention with an x-ray system, having an x-ray source, an x-ray receiver and a control and monitoring unit, in accordance with the independent claim. Advantageous embodiments of the invention form the subject matter of the subclaims.

The x-ray system according to the invention adapts the procedure of the entire x-ray recording and processing processes of one or a number of x-ray recordings by means of the control and monitoring unit, which is designed to be mobile and portable and comprises means for controlling and monitoring the x-ray system. All process steps, for instance the radiation trigger, the image acquisition, the image editing (post-editing) and image processing or image assessment, can be controlled and monitored by means of the portable control and monitoring unit. By the operator carrying the portable control and monitoring unit him/herself, all process steps can be implemented in an effortless and particularly quick fashion in any operator position required for the respective application or particularly advantageous therefore and in a portable control and monitoring unit.

According to one embodiment of the invention, the portable control and monitoring unit comprises a computing unit and a data storage device. This can be a computer or a PDA (Personal Digital Assistant) for instance. The portable control and monitoring unit advantageously comprises means for data management, which are operated together with the computing unit and the data storage device, in particular in the form of software. According to a further embodiment of the invention, the portable control and monitoring unit comprises means for image processing, in the form of an image processing unit for instance.

For improved monitorability of the process steps, the portable control and monitoring device comprises means for outputting and/or displaying imaging or system data, in particular in the form of at least one display. The portable control and monitoring unit expediently comprises means for inputting data and/or instructions. Input means of this type can take the form of control buttons or a touch-sensitive screen (touch screen, touch panel).

According to a further embodiment of the invention, the portable control and monitoring unit comprises bidirectional, wireless control and/or data connections to system-internal and/or system-external components. This ensures a comprehensive controllability of the system components and a two-way data exchange without any cables to get in the way.

Advantageously, the portable control and monitoring unit comprises at least one handle in order to make the portable control and monitoring unit particularly easy and convenient for operators to carry around with them.

BRIEF DESCRIPTION OF THE DRAWINGS

The invention as well as further advantageous embodiments according to the features of the subclaims are described below in further detail with reference to schematic representations of exemplary embodiments in the drawing, without the invention hereby being restricted to these exemplary embodiments, in which;

FIG. 1 shows an x-ray system having a stationary control and monitoring unit according to the prior art;

FIG. 3 shows a further x-ray system according to the invention having a mobile and portable control and monitoring unit;

DETAILED DESCRIPTION OF THE INVENTION

Figure 2:
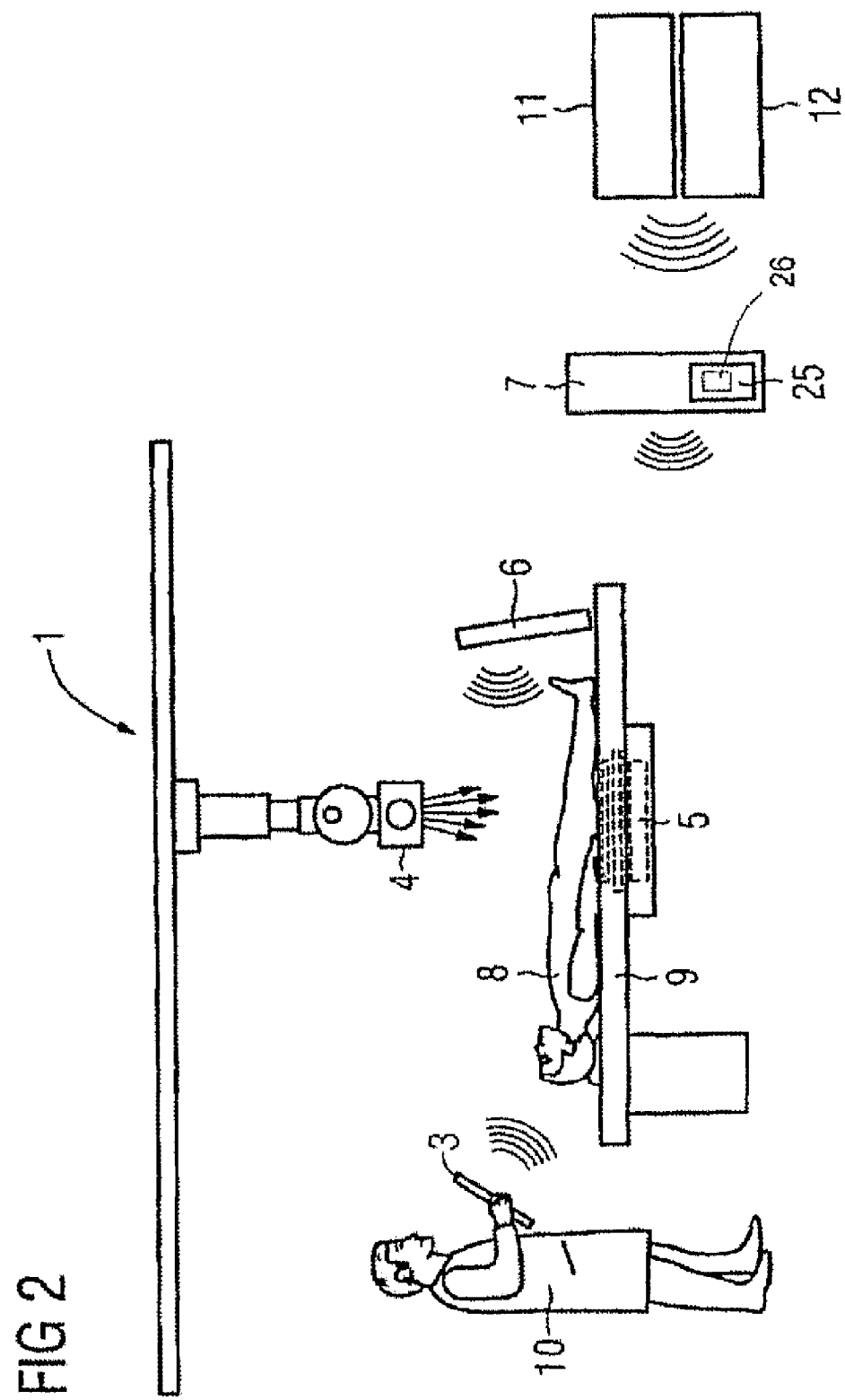
FIG. 2 shows an inventive x-ray system having a mobile and portable control and monitoring unit.

FIG. 1 shows a known x-ray system 30, which comprises at least one x-ray detector, for instance a permanently installed flat panel detector 5 and a stationary control unit 13 as its most important components. The known x-ray system 30 is provided to x-ray a patient 8, with the control and monitoring being carried out by an operator 10. The x-ray system 30 is frequently permanently installed in an examination room. The stationary control unit 13 furthermore contains an x-ray generator 7, which supplies the x-ray source 4 and an electronics assembly 25 accommodated therein. A permanently installed flat panel detector 5 can be integrated in a patient table 9 for instance or can be affixed to a support. Furthermore, x-ray systems are also known, which have a moveable equipment trolley or a mobile x-ray detector, such as described in DE 101 18 745 C2 for instance.

FIG. 2 and FIG. 3 show an inventive x-ray system 1 and a further inventive x-ray system 2, which, in addition to the x-ray source 4 and a stationary x-ray detector 5 or a portable x-ray detector 6, comprise a mobile and portable control and monitoring unit 3. An x-ray generator 7 is provided to supply the x-ray source 4, said x-ray generator 7 additionally being able to contain an electronics assembly 25. The portable control and monitoring unit 3 is carried by the operator 10 and is used to control and monitor the x-ray recording process and processing technique.

If required, the operator 10 with the portable control and monitoring unit 3 can retain his/her position next to the patient 8 and simultaneously operate the x-ray system. This can be necessary for instance in the case of intensive care patients or children or in order to demonstrate an x-ray image or its post-editing to the patient 8. On the other hand, the operator with the portable control and monitoring unit can if necessary also retire behind a radioprotective screen, or stay in any other position.

Figure 4:
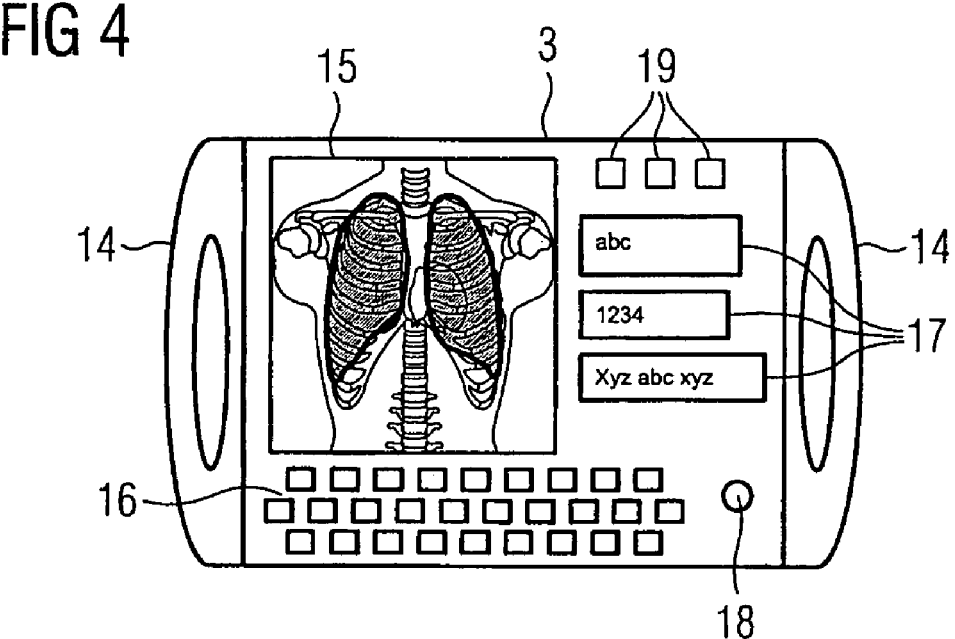
FIG. 4 shows a top view onto a portable control and monitoring unit having handles.
Figure 5:
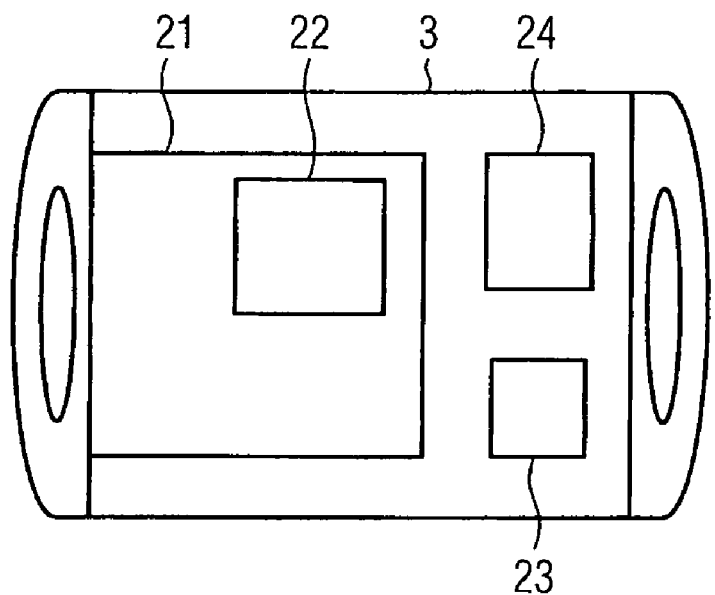
FIG. 5 shows a sectional view through a portable control and monitoring unit according to FIG. 4.

FIG. 4 and FIG. 5 show the portable control and monitoring unit 3 in an enlarged form, with FIG. 4 showing an exterior view and FIG. 5 an interior view. On the exterior, the portable control and monitoring unit 3 comprises a display 15, a first input field 16, a second input field 19, different indicators 17, a button 18 and two handles 14 on the exterior, which could be part of a housing accommodating the control and monitoring unit 3.

The display 15 and indicators 17 allow different patient or system information to be reproduced and/or x-ray images to be displayed. The input fields 16, 19, and the button 18 allow data and instructions to be input into the x-ray system. The first input field 16 is formed for instance from a touch screen keyboard. The button 18 can be used such that by activating it, an incidence of x-rays to the patient 8 is triggered. All functions of the x-ray system can be controlled by way of the input fields 16, 19 and button 18, thus the mechanical movement of the x-ray source is triggered for instance, parameters such as the radiation dose are adjusted and the x-ray detector is switched to receiving mode and an image correction of a read-out x-ray image is carried out.

Within its housing, the portable control and monitoring unit 3 has the intelligence of the x-ray system, in other words a computing and storage unit 21, an image processing software 22, a power supply unit 23 and a transmit and receive unit 24 for the wireless transmission and receipt of signals. The computing and storage unit 21 is designed in the form of a computer for instance, which features software for data management purposes. The image processing 22 can be similarly embodied as image processing software stored on the computing and storage unit 21, as shown in FIG. 5, or it can be embodied as a separate image processing unit.

Imaging data supplied by the x-ray detector is post-edited by means of the image processing software 22, by correcting artifacts, defects or noises from the x-ray imaging data for instance. The power supply unit 23, which can be designed as a battery, rechargeable battery, fuel cell or solar cell for instance, supplies the portable control and monitoring unit 3 with voltage, thereby ensuring independent operation.

The transmit and receive unit 24 communicates wirelessly and bidirectionally with the further modules of the x-ray system, such as the x-ray source 4, the x-ray detector 5 and the generator 7, in order to transmit and receive control commands, system data and imaging data. To this end, the x-ray source 4, x-ray detector 5 and generator 7 can likewise comprise transmitting and receiving means 26 for wireless data transmission. The wireless data transmission can be carried out for instance by means of radio communication, infrared or WLAN. By way of the transmit and receive unit 24, the portable control and monitoring unit is furthermore connected to system-external databases such as for instance a Picture Archiving System via a first interface 11 or with a hospital-internal Radiology Information System (RIS) via a second interface 12.

According to a further embodiment of the invention, the x-ray detector assigned to the x-ray system is designed to be mobile and portable and features a wireless control and/or data connection to the portable control and monitoring unit 3. In this way, the x-ray detector can also be positioned in a flexible manner and adjusted to the requirements of the patient and the x-ray application. A portable x-ray detector can be formed by a portable flat panel detector 6 for instance.

The invention can be summarized as follows: For a simplified and particularly flexible control of an x-ray system 1, 2 having an x-ray source 4, an x-ray detector 5, 6 and a control and monitoring unit, the control and monitoring unit 3 is designed to be mobile and portable and comprises means for controlling and monitoring the x-ray system 1, 2. The portable control and monitoring unit 3 in particular comprises a computing unit, a data storage device, means for data processing, means for outputting and displaying imaging or system data and means for inputting data and/or instructions.

The invention claimed is:

1. An x-ray system for recording an x-ray image of a patient, comprising:
an x-ray source;
an x-ray detector positioned to receive radiation from the x-ray source;
an x-ray generator configured to supply the x-ray source; and
a wireless handheld control and monitoring unit,
wherein the x-ray generator comprises an electronics assembly, the x-ray generator and the x-ray detector each comprising a transmit and receive unit for communicating wirelessly and bidirectionally with the wireless handheld control and monitoring unit, thereby enabling transmission of control commands, system data and imaging data, and
wherein the wireless handheld control and monitoring unit comprises a display suitable for display of x-ray image data, configured to wirelessly and bidirectionally communicate with the x-ray generator and the x-ray detector to transmit system data and imaging data and to control and monitor the x-ray system, wherein the wireless handheld control and monitoring unit is configured (i) to effect a wireless data connection with a database separate from the system, which database contains picture data or an information system, to retrieve data from the database and (ii) to display the data on the display of the wireless handheld control and monitoring unit.

2. The x-ray system as claimed in claim 1, wherein the wireless control and monitoring unit comprises a computing unit and a data storage device.

3. The x-ray system as claimed in claim 1, wherein the wireless control and monitoring unit comprises an image processor that processes a recorded image.

4. The x-ray system as claimed in claim 1, wherein the wireless control and monitoring unit comprises a device that outputs and displays the image or system data.

5. The x-ray system as claimed in claim 1, wherein the wireless control and monitoring unit comprises a device that inputs an instruction or data.

6. The x-ray system as claimed in claim 1, wherein the wireless control and monitoring unit comprises a device for data management.

7. The x-ray system as claimed in claim 1, wherein the wireless control and monitoring unit comprises a handle.

8. The x-ray system as claimed in claim 1, wherein the wireless control and monitoring unit comprises an integrated power supply unit.

9. The x-ray system as claimed in claim 1, wherein the x-ray detector is mobile and portable and comprises a wireless control or data connection that connects to the wireless control and monitoring unit.

10. The x-ray system as claimed in claim 1, wherein the wireless control and monitoring unit comprises a component selected from the group consisting of: a display unit, an indicator, an input field, a button, and a handle.

11. The x-ray system as claimed in claim 10, wherein the button triggers an incidence of x-rays to the patient.

12. The x-ray system as claimed in claim 1, wherein the wireless control and monitoring unit comprises a component selected from the group consisting of: a computing and storage unit, an image processing software, a power supply unit, and a transmit and receive unit.

13. The x-ray system as claimed in claim 12, wherein the image processing software is stored in the computing and storage unit or in a separate image processing unit.

14. A method for monitoring and controlling an x-ray system, comprising:
   providing an x-ray source coupled to an x-ray generator;
   providing an x-ray detector;
   positioning the detector relative to the source for recording an x-ray image by the x-ray system;
   providing a mobile and portable wireless handheld control and monitoring unit, separate and apart from the x-ray generator, comprising a computing unit, a data storage device and a display;
   wirelessly and birectionally transmitting system data and imaging data between the mobile and portable handheld control and monitoring unit and the x-ray generator, and between the mobile and portable handheld control and monitoring unit and the x-ray detector:
   controlling and monitoring the x-ray system with the mobile and portable wireless handheld control and monitoring unit;
   providing a recorded x-ray image for observation on the display; and
   effecting a wireless data connection to a database containing picture data and an information system for wireless transmission of picture data and display thereof on the display.

15. The method of claim 14 further including display of x-ray image data.

16. The method of claim 14 further including editing of the recorded x-ray image with image processing software in the mobile and portable wireless handheld control and monitoring unit.

* * * * *